May 25, 1965 O. O. DUNHAM Plant Pat. 2,517
CHRYSANTHEMUM PLANT
Filed March 4, 1964
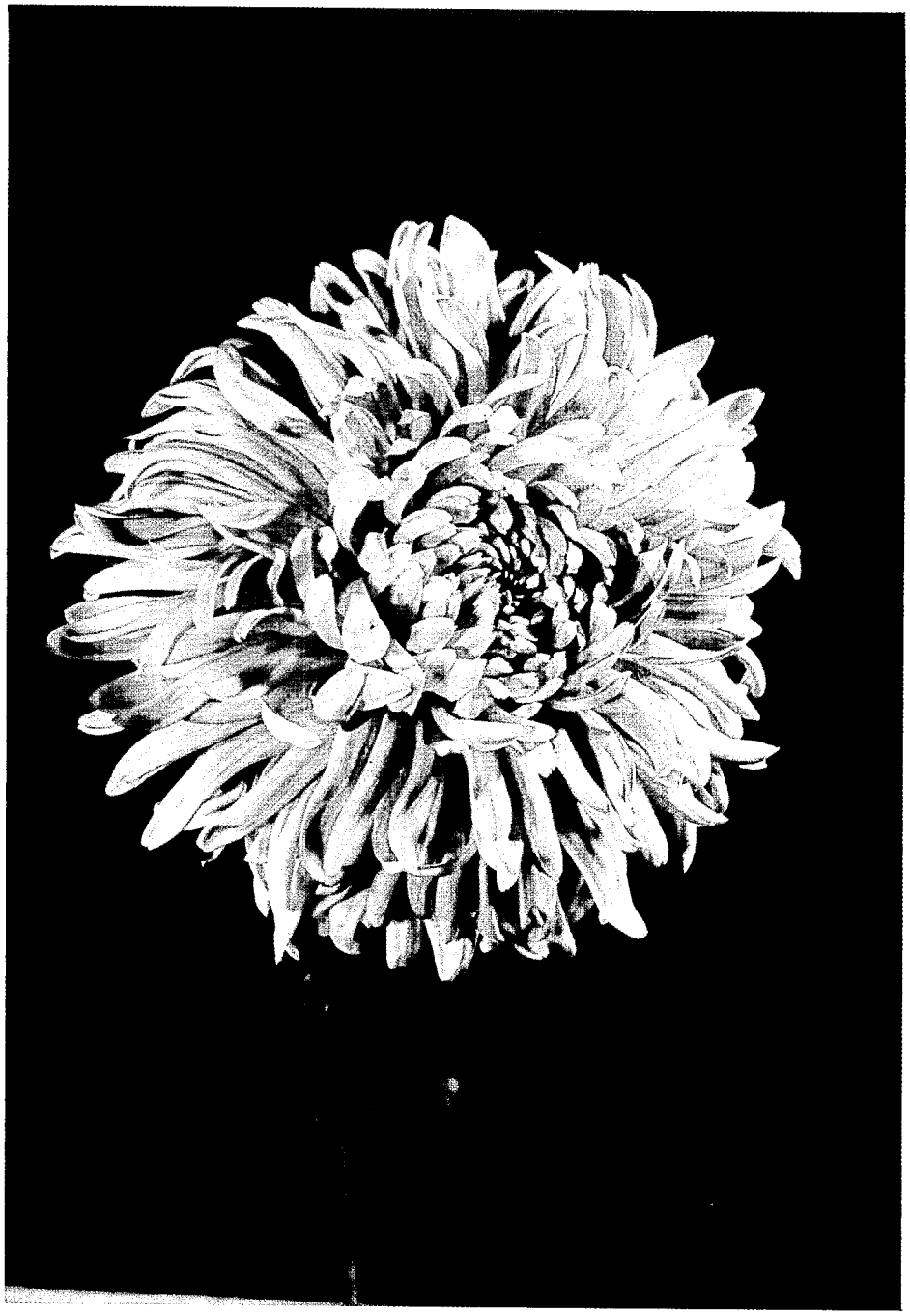
Inventor
O. O. Dunham
by Robb & Robb
attorneys United States Patent Office Plant Pat. 2,517
Patented May 25, 1965

2,517
CHRYSANTHEMUM PLANT

Orville O. Dunham, Niles, Mich., assignor to Stern's Nurseries, Inc., Geneva, N.Y., a corporation of New York Filed Mar. 4, 1964, Ser. No. 349,514
1 Claim. (Cl. Plt.—80)

My present invention comprises a new and distinct variety of chrysanthemum plant which I have developed by crossing a variety which I designate as #5350, which is unpatented and of my own origination, with a further variety likewise of my own origination and which I designate "Recreation" and likewise unpatented.

The object of my present invention has been to first of all take advantage of the earliness to bloom of the seed parent #5350, with certain color characteristics which are prominent in the pollen parent "Recreation."

One of the most notable differences between the new variety hereof, and either of the parents is the somewhat pearl-like luminescent color of the bloom in general aspect, providing a sort of luminous pink or pearl-like overall impression, which does not lend itself to specific color description but which as a basic consideration, is a Pale Purplish-Pink color with the luminescence emphasized therein.

Apparently this luminescence has perhaps resulted and is emphasized from the pollen parent "Recreation" which has a sort of gold-like impression, but in any event the instant variety is one which has features that neither of the parents have entirely and which I deem the best of parents for the purposes hereof.

This particular variety, has been the result of an extensive program of hybridization, and as a consequence thereof from careful selection and cross-breeding, I have developed this and other varieties, the instant variety being characterized by the Pale Purplish-Pink color of its blooms with pearl-like luminescence, the earliness and large size of its blooms, the tall strong stems, bushy plant habit and abundant Dark Yellowish-Green foliage.

More specifically, the blooms of my new variety are of the Pale Purplish-Pink color noted with luminescence, the closest description of the color being that noted as compared with the Nickerson Color Fan published by the Munsell Color Company.

The plant itself grows to a height of 20 to 24 inches, and is a large diameter plant with numerous blooms thereon.

The general color tonality is that of the pollen parent "Recreation," although a much more luminous and distinctive color distinguishes my new variety therefrom.

Under the conditions of culture previously mentioned, which have been understaken in the region of Niles, Michigan, plants of my new variety grow vigorously and continuously from mid-September to frost, the earliness to bloom of course deriving from the variety #5350.

My new variety when grown in the region of Niles, Michigan, blooms from mid-September until a killing frost and continuously.

My new variety has been asexually reproduced by cuttings in the vicinity of Niles, Michigan, observations from which the description set forth in detail hereinafter having taken place in mid-October.

My new variety has been found to retain its distinctive characteristics through successive asexual reproduction.

The accompanying drawing forming a part hereof shows a typical bloom of my new variety with some of the foliage, the colors being as nearly representative of the actual color of the plant as is possible in this type of illustration with the suggestion of luminescence disclosed and all being as nearly accurate as possible.

The following is a detailed description of my new variety of chrysanthemum plant, the color references being to the Nickerson Color Fan published by the Munsell Color Company:

*Description*

Parentage: Seedling.
*Seed parent.*—#5350 (unpatented).
*Pollen parent.*—"Recreation" (unpatented).
Classification: Botanic—*Chrysanthemum indicum.*

*Flower*

Blooming habit: Blooms from mid-September profusely until a killing frost.

Bud:
*Size.*—Large.
*Form.*—Short with flat top.
Not affected substantially by hot or wet weather.

Color:
*When sepals first divide.*—5RP 6/10 Deep Purplish-Pink.
*When petals begin to unfurl.*—2.5RP 6/10 Deep Purplish-Pink.
*When half blown.*—Inside of petals—2.5RP 7/8 Moderate Purplish-Pink. Reverse of Petals—5RP 8/5 Light Purplish-Pink.
*Sepals.*—Of no consequence.
*Calyx.*—Shape—funnel. Size—large and broad. Aspect—hairy.
*Peduncle.* — Length — medium. Aspect — rough. Strength—stiff and erect. Bud opens well and is not affected by hot or wet weather.

Bloom:
*Size.*—Very large.
*Average size when fully expanded.*—6 to 7 inches.
*Borne.*—In clusters, rounded.
*Stems.*—Long and strong.
*Form.*—When first open—cupped. Permanence—retains its form to the end.
*Petalage.*—Very double with innumerable petals under normal conditions.

Color:
*Center of flower.*—10P 6/9 Light Reddish-Purple.
*Outer petals.*—10P 8/5 Pale Purplish-Pink.
*Base of petals.*—7.5P 8/5 Very Pale Purple.
*Inside of petals.*—10P 7/7 Moderate Purplish-Pink.
*Reverse of petals.*—7.5P 9/2 Very Pale Purple.
*General tonality from a distance.*—7.5P 8/5 Very Pale Purple with luminescent sheen.
*Discoloration.*—General tonality at end of: First week—same as general tonality from a distance previously stated. Second week—retains same color. Third week—retains same color.

Petals:
*Texture.*—Thick and soft. Not affected by hot or wet weather.
*Appearance.*—Inside—velvety. Outside—satiny.
*Form.*—Oval.
*Arrangement.*—Irregular.
*Persistence.*—Hang on and dry.
*Fragrance.*—None.
*Lastingness.*—On the plant—very long. As cut flower—very long.

Genital organs:
*Stamens, anthers.*—Medium and few.
*Arrangement.*—Regular around styles.
*Stamens, filaments.*—Medium.
*Styles.*—Columnar.
*Length.*—Medium.
*Ovaries.*—All enclosed in calyx.

Plant:

*Form.*—Bush.

*Growth.*—Vigorous, upright and branching.

Foliage:

*Size.*—Large.

*Quantity.*—Abundant.

*Color.*—10GY 4/5 Dark Yellowish-Green.

*Shape.*—Lanceolate.

*Edge.*—Serrated.

*Serration.*—Single.

I claim:

A new and distinct variety of chrysanthemum plant, substantially as herein disclosed, characterized as to novelty by the Pale Purplish-Pink color of its blooms with pearl-like luminescence, the earliness and large size of the blooms, the tall, strong stems, bushy plant habit and the abundant Dark Yellowish-Green foliage.

No references cited.

ABRAHAM G. STONE, *Primary Examiner.*